(12) United States Patent
Beckers et al.

(10) Patent No.: US 6,655,846 B2
(45) Date of Patent: Dec. 2, 2003

(54) BALL BEARING AND BEARING ASSEMBLY

(75) Inventors: Johannes Beckers, Leutkirch (DE); Otto Gaile, Leutkirch (DE); Martin Engler, Leutkirch-Adrazhofen (DE); Edmund Foehr, Bad Wurzach-Haidgau (DE); Peter Moesle, Leutkirch-Diepoldshofen (DE)

(73) Assignee: MKL-Miniaturkugellager GmbH, Leutkirch (DE)

( * ) Notice: Subject to any disclaimer, the term of this patent is extended or adjusted under 35 U.S.C. 154(b) by 3 days.

(21) Appl. No.: 09/989,606

(22) Filed: Nov. 21, 2001

(65) Prior Publication Data

US 2002/0097935 A1 Jul. 25, 2002

(30) Foreign Application Priority Data

Nov. 21, 2000 (DE) .......................... 100 57 861

(51) Int. Cl.$^7$ ................................. F16C 33/60
(52) U.S. Cl. ....................... 384/513; 384/504
(58) Field of Search ................. 384/492, 504, 384/513, 516, 517, 518

(56) References Cited

U.S. PATENT DOCUMENTS

| | | | | |
|---|---|---|---|---|
| 3,056,636 A | * | 10/1962 | Mims ........................ | 384/517 |
| 3,376,084 A | | 4/1968 | McKee | |
| 3,417,963 A | | 12/1968 | Maverna | |
| 3,647,268 A | * | 3/1972 | Haines ....................... | 384/516 |
| 3,674,357 A | | 7/1972 | Ladin | |
| 3,738,719 A | * | 6/1973 | Langner ..................... | 384/517 |
| 4,071,954 A | | 2/1978 | Eugen | |
| 4,523,863 A | | 6/1985 | Okoshi | |
| 4,565,457 A | * | 1/1986 | Flander ...................... | 384/450 |
| 4,966,552 A | | 10/1990 | Gonser | |
| 5,273,413 A | * | 12/1993 | Wallin ........................ | 384/516 |
| 5,316,393 A | * | 5/1994 | Daugherty .................. | 384/517 |
| 5,499,832 A | * | 3/1996 | Iwamoto et al. ......... | 301/105.1 |
| 5,501,530 A | | 3/1996 | Nagai et al. | |
| 5,540,575 A | * | 7/1996 | Takano et al. ............. | 384/613 |
| 5,658,081 A | * | 8/1997 | Huang et al. ............... | 384/447 |
| 5,967,670 A | * | 10/1999 | Gabelli et al. ............. | 384/492 |
| 6,082,906 A | * | 7/2000 | Satou et al. ................ | 384/516 |
| 6,443,624 B1 | * | 9/2002 | Knepper et al. ........... | 384/492 |

FOREIGN PATENT DOCUMENTS

| | | |
|---|---|---|
| DE | 11 69 210 B | 4/1964 |
| DE | 24 54 079 A1 | 11/1974 |
| DE | 26 45 287 A1 | 10/1976 |
| DE | 31 40 091 A1 | 10/1981 |
| DE | 32 11 096 A1 | 3/1982 |
| DE | 42 24 695 A1 | 7/1992 |
| DE | 199 62 191 A | 12/1999 |
| EP | 0 807 761 A | 11/1997 |
| GB | 23 38 519 A | 6/1998 |
| JP | 2000-230547 | 1/2001 |

OTHER PUBLICATIONS

European Search Report dated May 6, 2003.
"SKF General Catalogue 4000 E," pp. 176–187, SKF, Printed by Carl Gerber GmbH XP002237259 (1989).
"Calculation of the Theoretical Life Expectancy of Ball Bearings," p. 24, Myonic Logistics.
*Hochleistungskeramik in FAG Waelzlagern, FAG Waelzlager*, Publ.No. WL 40 204 DA/80/11/90 p. 7, 17.

* cited by examiner

*Primary Examiner*—Thomas R. Hannon
(74) *Attorney, Agent, or Firm*—Breneman & Georges

(57) ABSTRACT

A ball bearing (6) and a bearing assembly are proposed which are intended especially for high-speed devices such as dental turbines, dental angle handpieces, turbomolecular pumps, etc., with balls (4) which are arranged between an inner ring (7) and an outer ring (8), which has substantially better anti-friction properties in rotating operation, especially during a startup phase, while simultaneously preventing the ball bearing or the bearing assembly being overloaded by the prestress or due to deviations in the geometry and and/or imprecision in assembly. This is achieved, according to the invention, by providing a device (4) to produce a tension force that is dependent on the speed (n).

20 Claims, 3 Drawing Sheets

BALL BEARING AND BEARING ASSEMBLY

The invention concerns a ball bearing and a bearing assembly, intended especially for high-speed devices such as dental turbines, dental angle handpieces, turbomolecular pumps, etc.

Up to now, high-speed devices such as dental turbines, dental angle handpieces, turbomolecular pumps, etc., have used high-precision ball bearings which are mounted on a shaft with the drive element between them. These bearings or bearing assemblies are installed with a fixed prestress which is applied by metal or elastomer spring elements. The action of the prestress makes the ball bearings free from play.

The prestress of the bearing causes a track offset. This track offset is achieved, for example in a double-row ball bearing, by giving the outer and inner rings different axial track separations. In bearing assemblies with two similar single-row ball bearings, the track offset is achieved especially by means of a corresponding shape of the ball bearing rings or by means of mechanical adjustment of the ball bearing rings and/or by means of spring elastic elements whose force flows through the balls and is received from the support, so that no resultant outward-acting force is produced.

However, such ball bearings or bearing assemblies have a disadvantage, which is that installation which puts a fixed prestress on the support produces a moment of friction in the bearing which acts even at the smallest speeds, that is in the startup range, and has a negative effect on it. Deviations in axial geometry of the bearing seat and/or imprecise assembly can significantly change the prestress force and thus can cause the bearing to have an excessively large or small prestress.

OBJECTS AND ADVANTAGES OF THE INVENTION

An object of the invention is to provide a ball bearing or a bearing assembly intended especially for high-speed devices such as dental turbines, dental angle handpieces, turbomolecular pumps, etc., which has substantially better anti-friction properties in rotating operation than conventional ones do, especially during a startup phase, while simultaneously preventing the ball bearing or the bearing assembly from being overloaded by the prestress or due to deviations in the geometry and or imprecision in assembly.

This object is solved, in a ball bearing and a bearing assembly of the type mentioned at the beginning, by the characterizing features of claims 1 and 12.

The measures mentioned in the subordinate claims make possible advantageous embodiments and further developments of the invention.

Thus, a ball bearing according to the invention is characterized in that at least one device is provided to produce a tension force that is speed-dependent.

A device according to the invention can be used, for example, to produce a ball bearing which has tensions of different magnitudes for different operating states. In rotating operation the ball bearing can have an adjustable tension force which changes continuously or incrementally, as a function of specified speed ranges. In particular this makes the ball bearing run in a more uniform manner.

It is advantageous to improve the startup behavior, that is, to shorten the startup phase, to provide a comparatively small tension force during the startup phase, so that a comparatively small drive force is needed. Among other things, this is advantageous for pneumatic or hydraulic drives such as are used for dental turbines, for example. The tension force of the required magnitude is achieved when operating speed is reached.

A defined axial displacement of the two rings relative to one another, i.e. axial play of the bearing is advantageously provided in the installed idle state. Establishing a defined axial play in the idle state represents a departure from the high-precision ball bearings developed up to now. However, the axial play makes possible a very small moment of friction at startup, which in turn makes it possible to reach operating speed especially quickly.

By contrast, a comparatively large tension on the ball bearing is also conceivable, especially to shorten a stopping phase of the bearing. Moreover, it can be advantageous to specify an appropriately large tension force in the idle state to hold the ball bearing.

It is advantageous for a maximum tension force to be provided when the maximum operating speed is reached. This makes the bearing comparatively stiff, especially at the beginning of a load. The comparatively large tension force simultaneously prevents, to the maximum possible extent, tilting of the outer ring, which produces an advantageous reduction in bearing noise. It is also possible to change the tension force as a function of the load.

It is preferable for the device according to the invention to be implemented by means of at least one tension element which can be tensioned to different extents, several connectable springs, etc. In particular, to determine the speed a sensor can be provided, e.g. an eddy current sensor, an optical sensor, etc.

In an advantageous further development of the invention an actuator is provided, especially a centrifugal governor, for centrifugally dependent open-loop or closed-loop control. This ensures that an advantageous continuous adjustment or control of the tension force to changing operating speeds can be achieved. This might also make it possible to do without other sensors.

In a particular embodiment of the invention, the device comprises at least part of the balls in the bearing. Thus, the balls rotating in the bearing can be used not only as rolling bodies, but also as a sensor and actuator element, due to the speed-dependent centrifugal forces acting on the balls. This means that the balls together with their tracks form a centrifugal governor and can simultaneously serve as tension elements, which makes it possible to implement an advantageous self-regulating and at the same time self-reinforcing tensioning of the ball bearing with comparatively small expense.

It is advantageous for a ball material to have a density greater than 5 g/cm$^3$. It is known in the art that the centrifugal force of a body is especially dependent on the density. Using a ball material with a density greater than 5 g/cm$^3$ produces, according to the invention, a comparatively large centrifugal force per ball. The centrifugal force can also be changed by advantageous adjustment of the ball diameter.

Here the tension force of the ball bearing at operating speed depends on the sum of the individual centrifugal forces. Performing numerous elaborate experiments made it possible to establish that especially a density greater than 5 g/cm$^3$ in corresponding high-speed ball bearings, such as, e.g., in miniature ball bearings for dental turbines, etc., makes it possible to produce prestress forces which substantially improve the stiffness of the support.

It is preferable for at least one ball in a bearing to consist essentially of steel which has a density of 7.7 g/cm$^3$. This has the advantage of using common ball bearing materials, which makes it possible to implement an embodiment of the device according to the invention that is especially economical.

In an advantageous further development of the invention, at least one ball consists essentially of zirconiumdioxide. Zirconiumdioxide has a density of about 6 g/cm$^3$, so that corresponding balls also can be provided to produce a tension force according to the invention.

In a special embodiment of the invention, each bearing row has at least one zirconiumdioxide ball, with the other balls in the bearing row consisting of steel. This combination, or a comparable combination of zirconiumdioxide balls and steel balls produces all different kinds of advantages in the operation of the bearing, due to the comparable physical properties of the materials zirconiumdioxide and steel. For example, zirconiumdioxide and steel have comparable moduli of elasticity and almost equal coefficients of linear expansion. Thus, outside and inside rings can be assembled into ball bearings with steel or $ZrO_2$ balls, without changing the track radii. The almost equal coefficients of linear expansion ensure that even when the corresponding ball bearing is under a temperature load no significant changes occur with respect to the anti-friction properties of the ball bearing.

The corresponding combination of balls advantageously even makes it possible for the comparatively hard zirconiumdioxide balls to press dust, abrasion, etc., into the tracks of the rings, which reduces the impairment of the bearings and causes a comparatively large increase in the life of the ball bearing. Here it is preferable to provide rings consisting of steel and/or yttrium-doped zirconiumdioxide balls.

Moreover, when zirconiumdioxide balls are used in separable ball bearings which consist essentially of steel it is advantageous that during installation the comparatively soft bump of the inside and outside ring which has to be overcome will not damage the balls. The comparatively slight damage of the bump here is not relevant for the running behavior of the bearing. Correspondingly positive features are also shown by silicon nitride balls, for example.

In an advantageous further development of the invention, at operating speed the tension force is $\geq 0.5\%$ of a dynamic radial load rating of the ball bearing. The German standard DIN/ISO 281 defines the dynamic radial load rating as the radial load, constant in the magnitude and direction, which a roller bearing can theoretically accept for a nominal life of $10^6$ revolutions.

The dynamic radial load rating is a bearing constant and is given in the product listings of rolling bearing manufacturers. The value of the dynamic radial load rating depends on many different factors, such as, e.g., the ball diameter, the track radius, the number of balls in a single-row bearing, or the number of balls per row in a multiple-row bearing, the number of rolling body rows in the bearing, the bearing type, or bearing design.

Numerous elaborate experiments have shown a corresponding dimensioning of the ball bearing according to the invention to be especially advantageous. Compared with a state-of-the-art ball bearing, a comparable ball bearing according to the invention can be operated at speeds well over 500,000 rpm.

In a special embodiment of the invention the ball bearing has an osculation between 1.04 and 1.35, with the osculation being the ratio of a track radius to the radius of the ball.

It is preferable for a spring element to provide decoupling, e.g. mechanical and/or electrical decoupling, of the ball bearing from a matching assembly to hold the ball bearing. An appropriate spring element makes it possible to achieve almost noiseless operation of the ball bearing, due to the mechanical decoupling of the ball bearing. It is preferable to use a mechanical spring element, air springing, etc., for this purpose.

The decoupling according to the invention of the ball bearing from at least one corresponding holding assembly is largely independent, especially of manufacturing and/or assembly tolerances of the ball bearing and the holding unit.

It is advantageous to provide a spring damping element to decouple the ball bearing. This means that, in addition to decoupling the ball bearing, it is also possible to achieve a mechanically stable damping of the support which can be provided above all for an advantageous adaptation to the load of the bearing in operation. For example, if the ball bearing according to the invention is used in a dental turbine or a dental angle handpiece, it is possible to adjust the springing and damping of the support to the individual working habits of the dentist.

A spring damping element can be provided by a coil spring, wave spring, or a disk spring, a rubber element, or by combinations of them or a comparable element. It is advantageous to provide at least one elastomeric element, which surrounds especially the front and sides of the outside ring. This makes it possible to achieve an especially simple design and assembly of the spring damping element according to the invention.

In principle, a corresponding spring or spring damping element is advantageous, even independent of the bearing tension according to the invention. It can simultaneously also be provided for electrical decoupling, i.e. insulation, between the ball bearing and the components held with it and the holding unit.

It is advantageous for the ball bearing to be made at least as a double-row ball bearing, with at least one so-called O-arrangement or a so-called X-arrangement being to provided. Here the inner ring with its tracks can be made as a shaft or axle, for example, and/or the outer ring can be made as a housing. This minimizes the danger of an offset or tilting when the tracks are assembled.

The multiple-row ball bearing according to the invention makes possible an advantageous design of the track offset, with especially the reduced axial play that is achieved in the idle state being smaller than the maximum axial play of the bearing and greater than zero. This causes centrifugal forces to act on the balls, due to the rotation of the support, so that especially their axial component presses the balls against the forces of friction into the bottom of the bearing's track, which makes the bearing's tension force speed-dependent, as provided by the invention.

It is preferable for a bearing assembly to be realized with at least two of the same type of single-row ball bearings according to the invention. This means that at least one O-arrangement or one X-arrangement is provided, in particular with it being possible to realize a track offset which in turn has a reduced axial play that is smaller than the maximum axial play and greater than zero.

SAMPLE EMBODIMENT

A sample embodiment of the invention is shown in the drawing and will be explained below using the figures.

THE FIGURES ARE AS FOLLOWS

Figure 1:
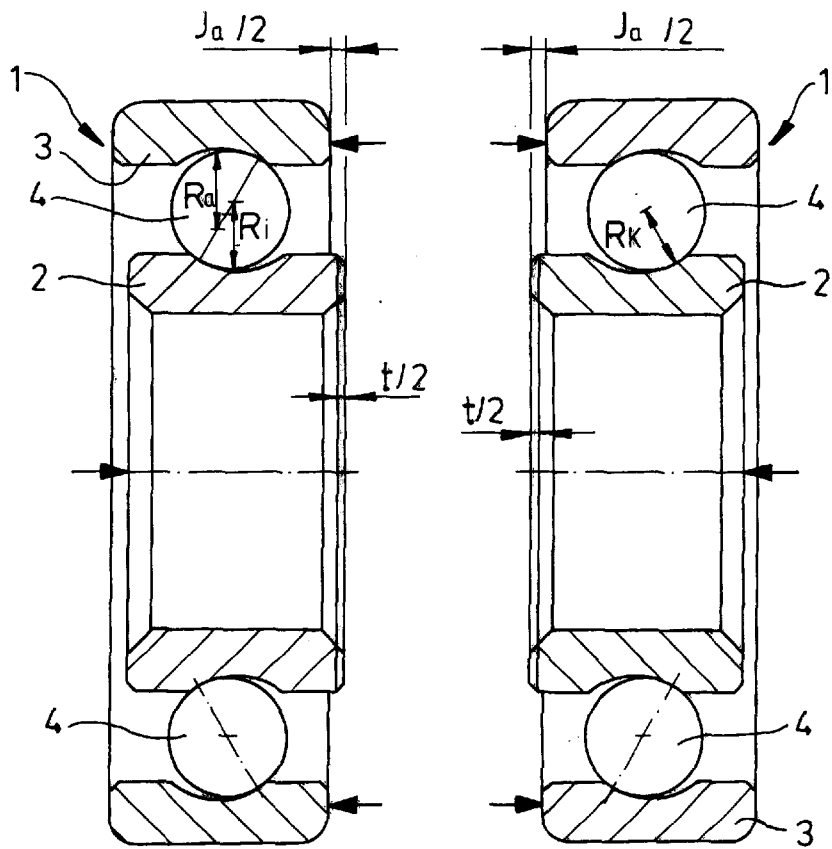
FIG. 1 is a schematic longitudinal section through two single-row ball bearings.

FIG. 1 shows two ball bearings 1, which comprise an inner ring 2, and outer ring 3, and several balls 4. The balls 4 have a ball radius $R_K$ and the inner ring 2 has a track radius $R_i$ and the outer ring 3 has a track radius $R_a$. According to the invention, ball bearing 1 has an osculation S between 1.04 and 1.25, with the osculation S being the ratio of the track radii $R_i$ and $R_a$ to the ball radius $R_K$.

A corresponding ball bearing 1 has the capability of shifting in the axial direction, the so-called axial play $J_a$. This means that the inner ring 2 can shift with respect to the outer ring 3 by half the axial play $J_a$ in each of the two opposite axial directions.

Figure 2:
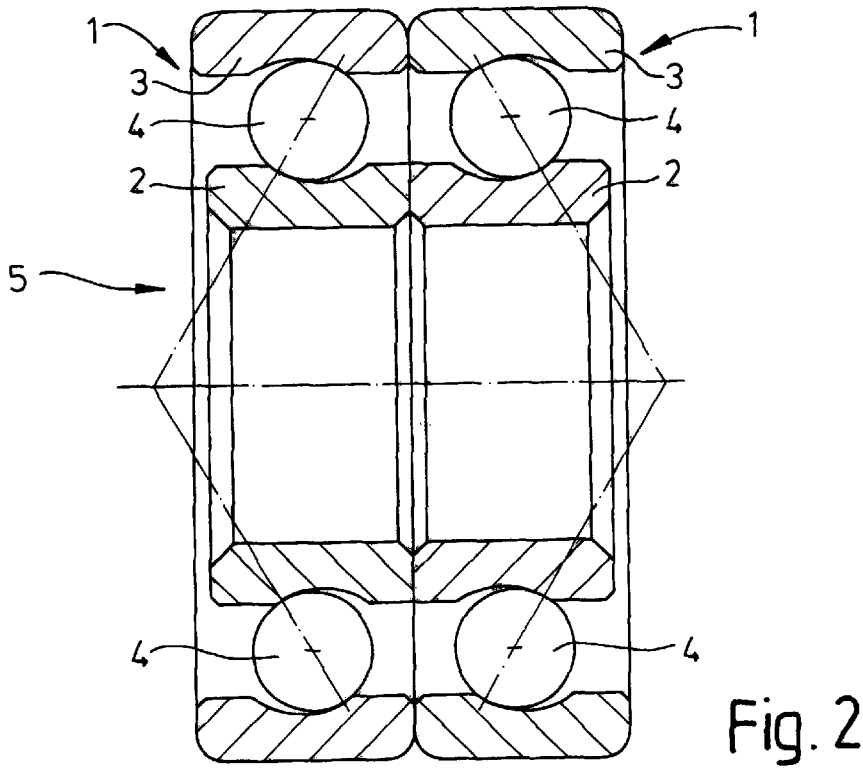
FIG. 2 is a schematic longitudinal section through a bearing assembly with two ball bearings according to FIG. 1.

According to the invention, half the amount t is removed from each inner ring 2, or t is removed from one of the two inner rings 2, so that when assembled as shown in FIG. 2, ball bearings 1 form a bearing assembly 5 with an O-arrangement, for example.

FIG. 2 shows the amount t smaller than the axial play $J_a$ of the ball bearings 1. According to the invention it is preferable to select the amount t to be greater than zero and smaller than the axial play $J_a$ of the ball bearing 1. This gives a bearing assembly 5 which, when assembled, has reduced axial play $J_a$ in the idle state and at a speed n>0 is prestressed with a tension force $F_v$ (see also FIG. 5). This achieves a bearing assembly 5 which has a comparatively rapid startup and a very high uniform maximum speed n, so that there will be no significant lag time between when the corresponding device is turned on and when the maximum operating speed is reached. Simultaneously, the higher maximum operating speed n makes it possible, for example, to improve processing by corresponding devices or possibly to open new areas of work for them.

Figure 5:
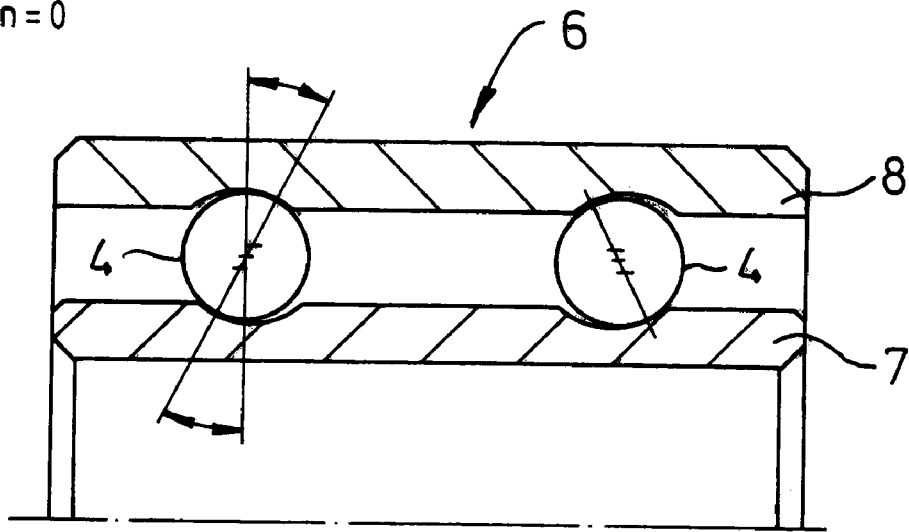
FIG. 5 is a schematic longitudinal section of a cutout of a double-row ball bearing in the idle state and in rotating operation state.
Figure 5:
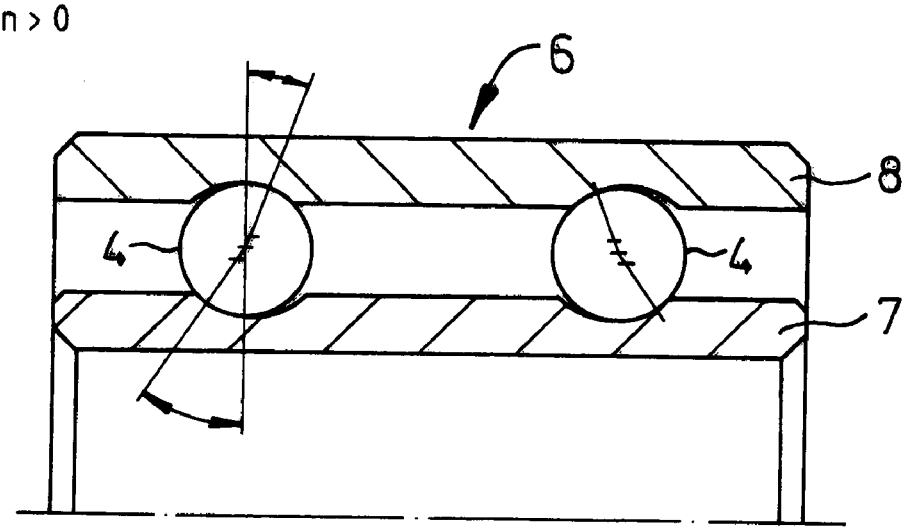

FIG. 5 shows a double-row ball bearing 6 both in the idle state, that is with an operating speed of n=0, as well as with an operating speed of n>0. Ball bearing 6 comprises an inner ring 7, and outer ring 8, and balls 4. Here the distance between the two tracks of inner ring 7 is somewhat smaller than the distance between the two tracks of outer ring 8, so that ball bearing 6 tends toward an O-arrangement. In principle here as well as for a bearing assembly 5 according to FIG. 2 an X-arrangement is also advantageous. Here the distance between the two tracks of inner ring 7 is somewhat greater than the distance between the two tracks of outer ring 8.

Figure 3:
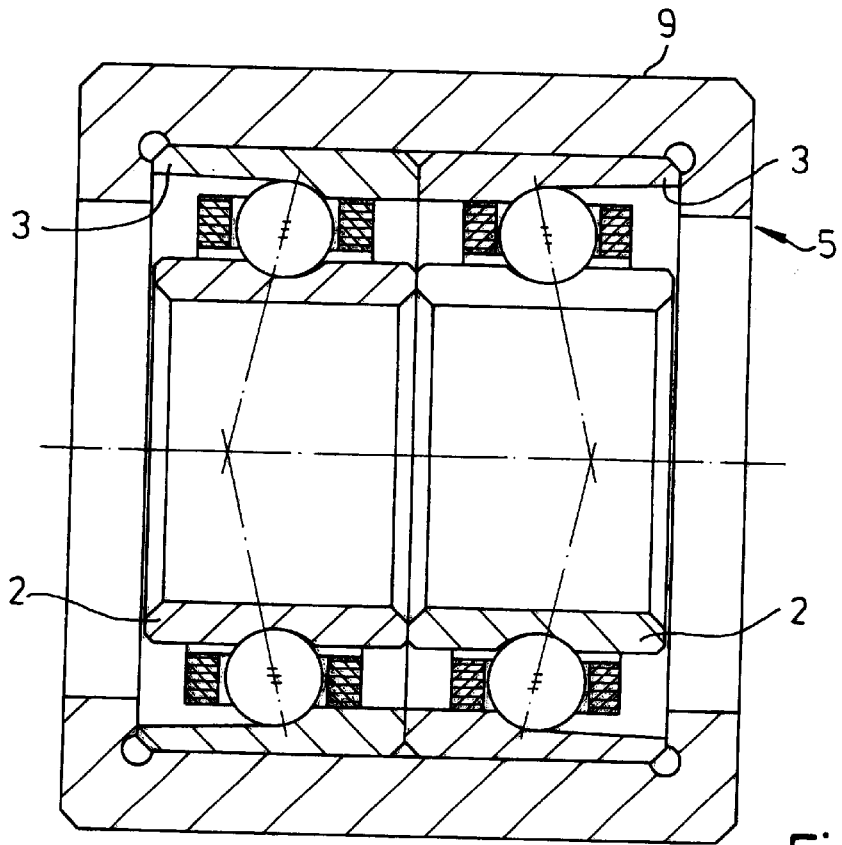
FIG. 3 is a schematic longitudinal section through a pair of bearings with two other ball bearings and a spring damping element.
Figure 4:
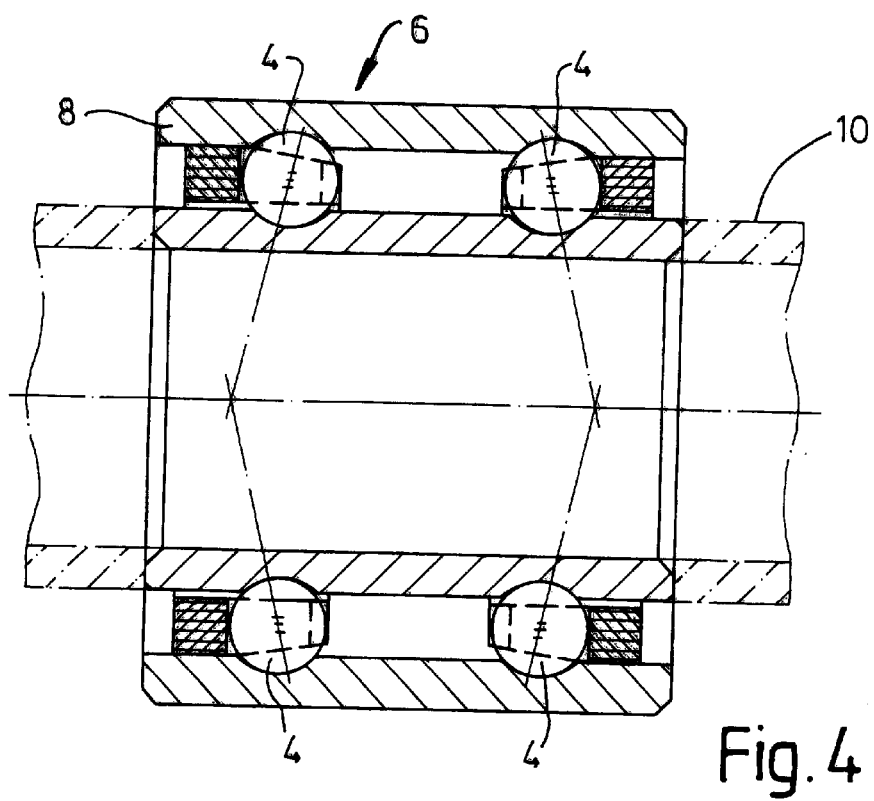
FIG. 4 is a schematic longitudinal section through double-row ball bearing.

FIGS. 3 and 4 show other variants of the bearing assembly 5 as well as of the double-row ball bearing 6. Bearing assembly 5 shown in FIG. 3 has an elastomeric element 9, which is provided to decouple bearing assembly 5. Elastomeric element 9 substantially reduces the noise of bearing assembly 5 during operation. According to the invention elastomeric element 9 could consist, for example, of at least three O-rings, with it advantageously being possible to put two O-rings on the front and at least one-ring on the side of the outer ring.

Moreover, metal elements such as coil springs, wave springs, etc., can also be used as spring damping elements.

All variants of the springing or spring damping of the ball bearing assembly 5 can be manufactured with comparatively large manufacturing tolerance, and can also be assembled for an individual ball bearing 1.

According to the invention the double-row ball bearing 6 can have, as its inner ring, a hollow shaft or a solid shaft 10 with two corresponding tracks.

In particular, all variants according to the invention of ball bearings 1, 6 as well as of bearing assembly 5 have, at an operating speed n, a tension force $F_v$ which is $\geq 0.5\%$ of a dynamic radial load rating $C_r$ of the ball bearing 1, 6 or of bearing assembly 5, i.e. $F_v/C_r \geq 0.5\%$. Thus, a ball bearing 1, 6 according to the invention or a bearing assembly 5 according to the invention can reach a maximum operating speed n of well over 500,000 rpm.

The material used for ball 4 is steel or zirconiumdioxide. Here it is possible to provide one zirconiumdioxide ball with several steel balls per bearing row. The comparatively hard zirconiumdioxide ball presses, for example, abrasion, dust, etc., into the track of the inner ring 2, 7 and/or the outer ring 3, 8, which are preferably made of steel. This has a positive effect on the life of the ball bearing 1, 6 according to the invention as well as of bearing assembly 5.

List of Reference Numbers and Abbreviations:

| | |
|---|---|
| 1 | Ball bearing |
| 2 | Inner ring |
| 3 | Outer ring |
| 4 | Ball |
| 5 | Bearing assembly |
| 6 | Ball bearing |
| 7 | Inner ring |
| 8 | Outer ring |
| 9 | Elastomeric element |
| 10 | Shaft |
| S | Osculation |
| $R_i$ | Track radius |
| $R_a$ | Track radius |
| $R_K$ | Ball radius |
| $J_a$ | Axial play |
| t | Amount removed |
| n | Speed |
| $F_v$ | Tension force |
| $C_r$ | Load rating |

What is claimed is:

1. A ball bearing (1, 6) adapted for a high-speed device having balls (4) which are arranged between an inner ring (2, 7) and an outer ring (3, 8), wherein the improvement comprises balls (4) having an adjustable speed-dependent tension-force (Fv) produced by centrifugal forces acting on the balls (4) to tension the balls (4) in a ball bearing (1, 6), and wherein there is a defined axial play in the idle state of the ball bearing.

2. The ball bearing (1, 6) according to claim 1, further comprising an actuator for centrifugally dependent open-loop or closed-loop control of the ball bearing.

3. The ball bearing (1,6) according to claim 1 or 2, wherein the material forming said balls has a density greater than 5 g/cm³.

4. The ball bearing (1,6) according to claim 1 or 2, wherein at least one ball (4) consists essentially of steel.

5. The ball bearing (1, 6) according to claim 1, wherein the balls (4) are adapted for use as a sensor and actuator element.

6. The ball bearing (1, 6) according to claim 1, wherein at least one ball (4) consists essentially of zirconium dioxide.

7. The ball bearing (1, 6) according to claim 1, wherein for an operating speed (n) the tension force (Fv) is greater than or equal to half of one percent of a dynamic radial load rating (Cr) of the ball bearing.

8. The ball bearing (1, 6) according to claim 1, wherein the ball bearing (1, 6) has an osculation S between 1.04 and 1.35, with the osculation S being the ratio of a radius (Ri, Ra) of the track to the radius of the ball (Rk).

9. The ball bearing (1, 6) according to claim 1, wherein the ball bearing (1, 6) is made at least as a double-row ball-bearing (6), with an O-arrangement or an X-arrangement being provided.

10. The ball bearing (1, 6) according to claim 1, further comprising a spring element (9) to decouple the ball-bearing (1, 6) from a unit for holding the ball-bearing (1, 6).

11. The ball bearing (1, 6) according to claim 1, further comprising a spring damping element (9) to decouple the ball-bearing (1, 6) from a unit for holding the ball-bearing (1, 6).

12. The ball bearing (1, 6) according to claim 1, further comprising a bearing assembly (5) with at least two single-row ball bearings.

13. The ball bearing (1, 6) according to claim 12, wherein said bearing assembly (5) is provided in an X-arrangement.

14. The ball bearing (1, 6) according to claim 12, wherein said bearing assembly (5) is provided in an O-arrangement.

15. A ball bearing and bearing assembly comprising:
   (a) an inner ring having a track with a radius Ri;
   (b) an outer ring having a track with a radius Ra, said inner ring and said outer ring combining to form a race;
   (c) at least one ball disposed in said race having a radius Rk;
   (d) a defined axial play (JA) so that said inner ring can shift with respect to said outer ring by one-half of said axial play (JA): and
   (e) a speed dependent tension force Fv between said at least one ball and said race resulting from an osculation S of about 1.04 to 1.35.

16. The ball bearing and ball bearing assembly of claim 15, wherein said at least one ball is a plurality of balls, each one of said plurality of balls having a density of greater than 5 g/cm$^3$.

17. The ball bearing and ball bearing assembly of claim 15, further comprising a spring or elastomeric element to decouple the bearing assembly.

18. A ball bearing assembly comprising:
   (a) a race for a ball having a first confronting surface with a curvilinear radius Ri and a second confronting surface with a curvilinear radius Ra wherein Ri and Ra are of different curvilinear radii;
   (b) a plurality of balls disposed in said race with each of said plurality of balls having a tension force Fv in said race;
   (c) means for axially shifting said first confronting surface with respect to said second confronting surface to impart a speed dependent tension force Fv by centrifugal forces acting upon said plurality of balls; and
   (d) a defined axial play (JA) so that said inner ring can shift with respect to said outer ring by one-half of said axial play (JA) in each of two opposite directions.

19. A ball bearing (1, 6) adapted for a high-speed device having balls (4) which are disposed between an inner ring (2, 7) and an outer ring (3, 8), wherein the improvement comprises having a speed dependent preloaded force Fv to preload the ball bearing (1, 6) generated by centrifugal forces acting upon said inner ring, said outer ring and said balls (4), and wherein the ball bearing (1, 6) has a defined axial play when in an idle state to provide a shift between said inner ring and said outer ring in opposite axial directions.

20. A ball bearing and bearing assembly comprising:
   (a) an inner ring having a track with a radius Ri;
   (b) an outer ring having a track with a radius Ra, said inner ring and said outer ring combining to form a race;
   (c) at least one ball disposed in said race having a radius Rk; and
   (d) a speed dependent tension force Fv between said at least one ball and said race resulting from an osculation S of about 1.04 to 1.35,
   wherein said inner ring shifts with respect to said outer ring in an opposite axial direction.

* * * * *